United States Patent [19]
Futaesaku et al.

[11] Patent Number: 5,502,207
[45] Date of Patent: Mar. 26, 1996

[54] ALKENYL-SUBSTITUTED BISNADIMIDES, PROCESS FOR MANUFACTURING THE SAME, PROCESS FOR CURING THE SAME, AND ADHESIVES AND COATING MATERIALS UTILIZING THE SAME

[75] Inventors: Norio Futaesaku; Hideo Fukuda, both of Ichihara; Yoshiharu Itou, Sodegaura; Hiromitsu Baba; Isao Maruyama, both of Ichihara, all of Japan

[73] Assignee: Maruzen Petrochemical Co., Ltd., Japan

[21] Appl. No.: 288,592

[22] Filed: Aug. 10, 1994

[30]   Foreign Application Priority Data

Aug. 13, 1993  [JP]  Japan ................... 5-222258
Apr. 18, 1994  [JP]  Japan ................... 6-104821

[51] Int. Cl.[6] ............ C07D 209/76; C08F 222/40
[52] U.S. Cl. ........................ 548/435; 526/262
[58] Field of Search ................. 548/435; 526/262

[56]      References Cited

U.S. PATENT DOCUMENTS

| | | | |
|---|---|---|---|
| 4,515,962 | 5/1985 | Renner | 548/435 |
| 4,579,916 | 4/1986 | Schmid et al. | 525/502 |
| 4,604,437 | 8/1986 | Renner | 526/262 |
| 4,666,997 | 5/1987 | Renner et al. | 525/502 |
| 4,678,849 | 7/1987 | Liu et al. | 526/259 |
| 4,709,047 | 11/1987 | Renner et al. | 548/435 |
| 4,728,742 | 3/1988 | Renner et al. | 548/435 |
| 4,777,236 | 10/1988 | Kramer | 528/322 |
| 4,778,898 | 10/1988 | Vonlanthen et al. | 548/415 |
| 4,885,346 | 12/1989 | Kramer et al. | 525/426 |
| 4,966,923 | 10/1990 | Banks et al. | 522/167 |
| 5,120,857 | 6/1992 | Kramer et al. | 548/435 |

OTHER PUBLICATIONS

Japanese Patent Laid-open No. Sho 63 (1988)—170358—abstract.
Japanese Patent Laid-open No. Sho 63 (1988)—310884—abstract.

Primary Examiner—Joseph L. Schofer
Assistant Examiner—Wu C. Cheng
Attorney, Agent, or Firm—Melvin I. Stoltz

[57]      ABSTRACT

An alkenyl-substituted bisnadimide represented by the following formula [1]:

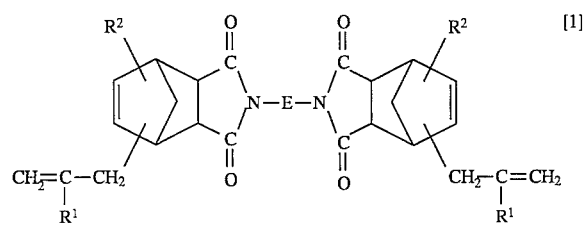

[wherein $R^1$ and $R^2$ individually represent a hydrogen atom or a methyl group, and E is an alkylene.phenylene group or an alkylene.phenylene.alkylene group represented by the following formula [2]:

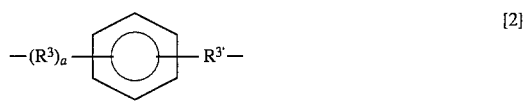

(wherein a is an integer of 0 or 1, and $R^{3'}$ individually represent a $C_1$–$C_4$ alkylene group or a $C_5$–$C_8$ cycloalkylene group)], a process for the preparation of the same and a process for curing the same are disclosed. Further, an adhesive material and a coating material containing the bisnadimide as a curing component are also disclosed. A cured material obtaind from the bisnadimide has excellent heat resistance, mechanical strength, toughness, adhesion property to many kinds of substrates, and so on. The adhesive material shows excellent heat resistance and the coating material shows excellent boiling water resistance.

5 Claims, 8 Drawing Sheets

ALKENYL-SUBSTITUTED BISNADIMIDES, PROCESS FOR MANUFACTURING THE SAME, PROCESS FOR CURING THE SAME, AND ADHESIVES AND COATING MATERIALS UTILIZING THE SAME

BACKGROUND OF THE INVENTION

1. Field of the Invention

The present invention relates to a novel alkenyl-substituted bisnadimide, which is a thermosetting resin exhibiting excellent processability, heat resistance, mechanical strength, electrical characteristics, a process for manufacturing said alkenyl-substituted bisnadimide, and a process for curing the same. Further, the present invention also relates to an adhesive and a coating material comprising said novel alkenyl-substituted bisnadimide as a curing component. The novel alkenyl-substituted bisnadimide is useful as a laminating material, a cast molding material, a molding material, a coating material, a paint, an adhesive, a filler, and a matrix resin for composite resins in which glass or carbon fibers are used as a reinforcing material. In particular, this alkenyl-substituted bisnadimide exhibits superior heat resistance for a long period of time when used as an adhesive, and exhibits excellent resistance to boiling water when used as a coating material.

2. Description of the Prior Art

There is an increasing demand for high performance and high functional materials along with the advance of science and technology. A great number of materials are being developed in order to satisfy this demand. Among these materials, applications of thermosetting resins have expanded to cover wide areas, including the areas of structural materials for air crafts and the like, and the areas of electronic or electrical materials, such as packaging materials for semiconductors, laminating materials, coating materials, and adhesives. A characteristic particularly demanded of such thermosetting resins is excellent heat resistance. Further, various high performance polymers, which are generally called super engineering plastics, such as polyether ketones, polyphenylene sulfides, and polyimides, have been introduced to the market. Among these, polyimides are materials of which the demand is expected to expand in future.

Bisnadimide compounds possessing norbornene rings at the both ends and aromatic groups in the molecule have heretofore attracted a great deal of attention as a raw material for addition-type polyimide resins with extremely high heat resistance. Some of them have already been used as a matrix of forerunner composite materials. The bisnadimide compounds, however, have drawbacks in their high melting point, the insufficient solubility in solvents, and the poor reactivity. These render these compounds difficult to handle and require severe reaction conditions to polymerize (e.g., 300° C. or higher molding temperature). The reactions under severe conditions not only promote polymerization reaction but also partly accompany a reverse Diels-Alder reaction which produces volatile cyclopentadiene. The cyclopentadiene vapor causes a great number of boids to be produced in the molded products, impairing properties thereof. Therefore, the application of bisnadimide is considerably limited. Molding of a bisnadimide resin is therefore limited to a process using a high temperature under high pressure, such as the autoclave molding process, or it can only be used as a vanish produced by the oligomerization of raw materials of bisnadimide, i.e., a nadic anhydride or an ester thereof and a diamine, dissolved in a solvent.

Various processes for introducing suitable substituent groups to the norbornene ring of bisnadimide are investigated in order to eliminate these drawbacks in bisnadimide.

One of the processes is introducing alkenyl groups such as allyl group or methallyl group, and a number of proposals dealing with this process have been reported, e.g., U.S. Pat. Nos. 4,515,962, 4,579,916, 4,604,437, 4,666,997, 4,678,849, 4,709,047, 4,728,742, 4,777,236, 4,778,898, 4,885,346, 4,966,923, 5,120,857, Japanese Patent Laid-open No. Sho 63 (1988)-170358 and No. Sho 63 (1988)-310884, etc.

These proposals claim that the introduction of alkenyl groups, such as allyl group or methallyl group, lowers the melting point of the nadimide, increases its solubility in solvents, lowers curing temperature to a certain degree, and prevents production of volatile matters when the resin is cured, while without substantially injuring properties of the resulting cured resin. These alkenyl-substituted nadimides are thus considered to exhibit excellent processability, and their thermoset products are deemed to have superior heat resistance, mechanical strength, electrical characteristics, and chemical stability. These are thus useful in some degree as a laminating material, molding material, composite material, coating material, paint, or adhesive. However, these alkenyl-substituted nadimides are insufficient and still to be improved in their mechanical properties, especially in toughness, and in their adhesion characteristics to substrates.

In the field of heat resistant adhesives, thermosetting polyimides, such as bismaleimide, polyamino-bismaleimide (KERIMIDE, tradename, Ciba-Geigy AG), and triazine-modified bismaleimide (BT Resin, tradename, Mitsubishi Gas Chemical Company, Inc.), have been known conventionally. The alkenyl-substituted nadimides are also known to be usable as a heat resistant adhesive. These conventional imides, however, are still insufficient in their heat resistance when used as an adhesive for a long period of time at a high temperature.

Further, in the field of coating materials a number of thermosetting polyimides, including said alkenyl-substituted nadimides, are also known to be usable as coating materials. These conventional thermosetting polyimide type coating materials are insufficient in their resistance to boiling water, when applied to surfaces exposed to boiling water or high temperature steam, such as hot water boilers, boiling water tanks, and hot water pipes.

SUMMARY OF THE INVENTION

An object of the present invention is to provide a novel alkenyl-substituted bisnadimide, which can produce a thermoset resin which does not have the above-mentioned problems, and which exhibits improved mechanical strength, especially improved toughness, and excellent adhesion characteristics to substrates, while maintaining superior heat resistance and electrical characteristics inherently possessed by conventional alkenyl-substituted nadimide thermoset resins. The present invention further provides a process for manufacturing this alkenyl-substituted bisnadimide and a process for curing the same. Further, the present invention provides an adhesive which is well resistive to a high temperature of 250° C. or above for a long period of time and a coating material which exhibits excellent boiling water resistance.

We have undertaken extensive studies in order to achieve the above-mentioned objects and, as a result, have found that a cured product of a novel alkenyl-substituted bisnadimide containing a diamine component with a specific structure different from diamines conventionally used in the preparation of alkenyl-substituted nadimides exhibits unique characteristics as compared with cured products made from conventional alkenyl-substituted nadimides. That is, it has excellent mechanical strength, toughness, and adhesion characteristics to substrates, as well as improved heat resistance. We have further found that this novel alkenyl-substituted bisnadimide can provide an adhesive which exhibits excellent heat resistance at a high temperature for a long period of time and can provide a coating material which exhibits excellent boiling water resistance. These findings have led to the completion of the present invention.

Accordingly, the gist of the first invention resides in an alkenyl-substituted bisnadimide represented by the following formula [1]:

[wherein $R^1$ and $R^2$ individually represent a hydrogen atom or a methyl group, and E is an alkylene.phenylene group or an alkylene.phenylene.alkylene group represented by the following formula [2]:

(wherein a is an integer of 0 or 1, and $R^3$ and $R^{3'}$ individually represent a $C_1$–$C_4$ alkylene group or a $C_5$–$C_8$ cycloalkylene group)].

The gist of tile second invention resides in a process for preparing said alkenyl-substituted bisnadimide, which comprises reacting an alkenyl-substituted bicyclo [2.2.1]hept-5-ene-2,3-dicarboxylic acid anhydride derivative represented by the following formula [3]:

(wherein $R^1$ and $R^2$ individually represent a hydrogen atom or a methyl group) and a diamine of the following formula [4]:

[wherein E is an alkylene.phenylene group or an alkylene.phenylene.alkylene group represented by the following formula [2]:

(wherein a is an integer of 0 or 1, and $R^3$ and $R^{3'}$ individually represent a $C_1$–$C_4$ alkylene group or a $C_5$–$C_8$ cycloalkylene group)].

The gist of the third invention resides in a process for curing said alkenyl-substituted bisnadimide which comprises heating said alkenyl-substituted bisnadimide at 80°–400° C. for 0.001–30 hours in the absence or presence of a curing catalyst.

The gist of the fourth invention resides in an adhesive comprising said alkenyl-substituted bisnadimide as a curing component.

The gist of the fifth invention resides in a coating material comprising said alkenyl-substituted bisnadimide as a curing component.

DETAILED DESCRIPTION OF THE INVENTION

The alkenyl-substituted bisnadimide of formula [1] can be synthesized by the reaction of, an alkenyl-substituted bicyclo [2.2.1]hept-5-ene-2,3-dicarboxylic acid anhydride derivative, which is conventionally known to be used for the synthesis of alkenyl-substituted nadimides and represented by the following formula [3]:

wherein $R^1$ and $R^2$ individually represent a hydrogen atom or a methyl group (this compound is hereinafter referred to as alkenyl-substituted nadic acid anhydride derivative)], and a diamine having a specific structure and represented by the following formula [4]:

[wherein E is an alkylene.phenylene group or an alkylene.phenylene.alkylene group represented by the following formula [2]:

(wherein a is an integer of 0 or 1, and $R^3$ and $R^{3'}$ individually represent a $C_1$–$C_4$ alkylene group or a $C_5$–$C_8$ cycloalkylene group)].

Given as typical examples of alkenyl-substituted nadic acid anhydride derivatives of formula [3] are allyl-bicyclo[2.2.1]hept-5-ene-2,3-dicarboxylic acid anhydride, methallyl-bicyclo[2.2.1]hept-5-ene-2,3-dicarboxylic acid anhydride, allylmethyl-bicyclo[2.2.1]hept-5-ene-2,3-dicarboxylic acid anhydride, and methallylmethyl-bicyclo [2.2.1]hept-5-ene-2,3-dicarboxylic acid anhydride.

As the E group of the diamines represented by the formula [4], when the E group is phenylene.alkylene structure, for example, phenylene.methylene group (wherein phenylene group can be any one of o-, m- and p-configurations, hereinafter the same), phenylene.ethylene group, phenylene.trimethylene group, phenylene.tetramethylene group, phenylene.butylidene group, phenylene.s-butylidene group, phenylene.1-methylethylene group, phenylene.2-methylethylene group, phenylene.1,2-dimethylethylene group, phenylene.1,1-dimethylethylene group, phenylene.1,2-cyclopentylene group, phenylene.1,3-cyclopentylene group, phenylene.1,4-cyclopentylene group, phenylene.2-methyl-1,4-cyclopentylene group, phenylene.2,3-dimethyl-1,4-cyclopentylene group, phenylene.1,2-cyclohexylene group, phenylene.1,4-cyclohexylene group, phenylene.2methyl-1,3-cyclohexylene group, phenylene.3-methyl-1,4-cyclohexylene group, phenylene.3-ethyl-1,4-cyclohexylene group, phenylene.1,3-cycloheptylene group, phenylene.3-methyl-1,4-cycloheptylene group, phenylene.4-methyl-1,3-cycloheptylene group, phenylene.1,3-cyclooctylene group and phenylene.1,4cyclooctylene group can be cited. As the E group of the diamines represented by the formula [4], when the E group is alkylene.phenylene.alkylene structure, for example, o-, m- and p-xylylene group, methylene.phenylene.ethylene group, methylene.phenylene.trimethylene group, methylene.phenylene.1-methylethylene group, methylene.phenylene.2-methylethylene group, methylene.phenylene.1,2-dimethylethylene group, methylene.phenylene.1,4-cyclopentylene group, ethylene.phenylene.butylidene group, group, butylidene.phenylene.butylidene group, trimethylene.phenylene.s-butylidene group, trimethylene.phenylene.1,3-cyclooctylene group, 1,4-cyclopentylene.phenylene. 1,4-cyclopentylene group, 1,3-cyclooctylene.phenylene. 3-ethyl-1,4-cyclohexylene group, 1,3-cyclooctylene.phenylene.1,3-cyclooctylene group and 1,4-cyclohexylene.phenylene.1,3-cyclooctylene group can be cited. The aboves are illustrations only, and the E group of formula [4] is not limited to the above.

Synthesis of the alkenyl-substituted bisnadimide of formula [1] in the present invention can be carried out according to conventional processes for producing alkenyl-substituted nadimides.

Specifically, the alkenyl-substituted bisnadimide of formula [1] of the present invention can be prepared almost stoichiometrically by reacting said alkenyl-substituted nadic acid anhydride derivative and said diamine at 80°–220° C. for 0.5–20 hours in the absence or presence of a solvent.

Alternatively, it can be synthesized by a two step reaction, in which said alkenyl-substituted nadic acid anhydride derivative and said diamine are reacted in the presence of a solvent at a relatively low temperature first to produce an amic acid which is an intermediate of the imide, and then cyclization and imidation are carried out using a tertiary amine or, if necessary, a combination of a tertiary amine and nickel acetate, as a catalyst, and acetic anhydride or the like as a dehydration agent.

Benzene, toluene, xylene, methylnaphthalene, tetralin, chloroform, trichlene, tetrachloroethylene, chlorobenzene, dioxane, tetrahydrofuran, anisole, acetone, methyl ethyl ketone, methyl isobutyl ketone, acetophenone, N,N-dimethylformamide, dimethyl sulfoxide, N-methylpyrrolidone, and the like are given as examples of solvents usable in the synthesis.

The alkenyl-substituted bisnadimide of the present invention can be polymerized and cured by heating at 80°–400° C. for 0.001–30 hours. It is desirable to use a catalyst to complete the curing reaction at a relatively low temperature in a relatively short period of time.

As curing catalysts for use in the polymerization or curing of alkenyl-substituted bisnadimide of the present invention, (1) cationic catalysts, (2) onium salts, (3) organic peroxides, (4) organic compounds of transition elements, and so on can be cited.

As (1) the cationic catalysts of the above, for example, acids or Brønsted acids which can liberate protons, and esters thereof or amine complexes thereof, such as sulfuric acid, dimethyl sulfate, diethyl sulfate, aniline sulfate, sulfuric acide.pyridine complex, phosphoric acid, phosphorous acid, phenylphosphonic acid, phenylphosphinic acid, triethyl phosphate, dimethyl phosphate, diphenyl phosphate, phenyl phosphite, methanesulfonic acid, trifluoromethanesulfonic acid, benzenesulfonic acid, p-toluenesulfonic acid, p-toluenesulfonic acid.triphenylamine complex, pyridinium p-toluenesulfonate, pyridinium m-nitrobenzenesulfonate, α- or β-naphthalenesulfonic acid, methyl benzenesulfonate, methyl p-toluenesulfonate, ethyl p-toluenesulfonate, and N-(2-benzenesulfonylhydroxyethyl)-allyl-bicyclo[2.2.1]hept-5-ene- 2,3-dicarboximide (ANI-BsE); and for example, halide of Group II–V elements of Periodic Table showing Lewis acidity or their complexes with bases, or the like, such as boron trichloride, boron trifluoride, boron trifluoride.ether complex, boron trifluoride.piperazine complex, ferric chloride, nickel chloride, stannic tetrachloride, titanium tetrachloride, aluminium chloride, aluminium chloride.ether complex, aluminium chloride.pyridine complex, aluminium bromide, zinc chloride and antimony pentachloride can be cited.

As (2) the onium salts, for example, ammonium compounds, such as benzyl triethylammonium chloride, benzyltriethylammonium bromide, benzyltri-n-butylammonium chloride, benzyltri-n-butylammonium bromide, phenyltrimethylammonium bromide, tetra-n-butylammonium chloride, tetra-n-butylammonium perchlorate, tetraethylammonium tetrafluoroborate, m-trifluoromethylphenyltrimethylammonium bromide and tetra-n-butylammonium trifluoromethanesulfonate; phosphonium compounds, such as methyltriphenylphosphonium iodide, methyltriphenylphosphonium bromide, benzyltriphenylphosphonium chloride, tetraphenylphosphonium bromide and 3-bromopropyltriphenylphosphonium bromide; arsonium compounds, such as benzyltriphenylarsonium chloride, tetraphenylarsonium bromide and tetra-n-butylarsonium chloride; stibonium compounds, such as benzyltriphenylstibonium chloride and tetraphenylstibonium bromide; oxonium compounds, such as triphenyloxonium chloride and triphenyloxonium bromide; sulfonium compounds, such as triphenylsulfonium tetrafluoroborate, triphenylsulfonium hexafluoroarsenate, tri(p-methoxyphenyl)sulfonium hexafluorophosphate, tri-(p-tolyl) sulfonium tetrafluoroborate, dimethylphenacylsulfonium hexafluorophosphate, dimethylphenacylsulfonium tetrafluoroborate and diphenylphenacylsulfonium tetrafluoroborate; selenonium compounds, such as triphenylselenonium tetrafluoroborate, triphenylselenonium hexafluoroarsenate, triphenylselenonium hexafluoroantimonate and p-(t-butylphenyl)diphenylselenonium hexafluoroarsenate; stannonium compounds, such as triphenylstannonium chloride, triphenylstannonium bromide, tri-n-butylstannonium bromide and benzyldiphenylstannonium chloride; and iodonium compounds, such as diphenyliodonium chloride, diphenyliodonium bromide, diphenyliodonium perchlorate, diphenyliodonium tetrafluoroborate, diphenyliodonium hexafluoroarsenate, diphenyliodonium hexafluorophosphate, diphenyliodonium hexafluoroantimonate, (p-methoxyphenyl)phenyliodonium tetrafluoroborate, di(2-nitrophenyl)iodonium hexafluoroarsenate, di(p-tolyl) iodonium hexafluorophosphate and di(p-chlorophenyl)iodonium hexafluoroarsenate can be cited.

As (3) the organic peroxides, for example, di-t-butyl peroxide, di-t-amyl peroxide, dicumyl peroxide, t-butylcumyl peroxide, diacetyl peroxide, dipropionil peroxide, di-i-butyryl peroxide, benzoyl peroxide, succinic acid peroxide, t-butyl hydroperoxide, cyclohexyl hydroperoxide, cumene hydroperoxide, t-butylperoxy benzoate, t-butylperoxy pivalate, 1,1-di-t-butylperoxy cyclohexane, di(t-butylperoxy)isophthalate, t-butylperoxy maleate, t-butylperoxy isopropylcarbonate and 2,2-di-t-butylperoxy butane are cited.

As (4) the organic compounds of transition elements, for example, acetyl acetonates, organic carboxylic acid salts, metallocenes, alcoholates, chelate compounds and organometallic compounds of transition elements such as Ti, V, Cr, Mn, Fe, Co, Ni, Cu, Zr, Mo, Ru, Rh, La, Ce, Hf, Ta and W, and preferably acetyl acetonates of V, Mn, Fe and Ce can be cited. Incidentally, joint use of (3) the organic peroxides and (4) the organic compounds of transition elements is also applicable.

The amount of the curing catalyst used in the reaction can be determined from a wide range with no specific limitations, usually, from a range of 0.005–10% by weight, and preferably 0.01–5% by weight, of the amount of the alkenyl-substituted bisnadimide.

The alkenyl-substituted bisnadimides of the present invention can be used as a mixture of two or more bisnadimide compounds falling within the definition of the present invention, or they may be served for use as an oligomer.

The alkenyl-substituted bisnadimide of the present invention not only exhibits the same superior solubility in various solvents as conventional alkenyl-substituted nadimides, but also has more excellent heat resistance, mechanical strength, toughness, and adhesion properties to substrate than conventional alkenyl-substituted nadimides. They are directed to a variety of applications such as a laminating material, a cast molding material, a molding material, a coating material, a paint, an adhesive, a filler, and a matrix resin for composite resins using glass or carbon fibers as a reinforcing material.

Among the above applications, the alkenyl-substituted bisnadimides of the present invention are particularly suitable for use as an adhesive or a coating material. Among the alkenyl-substituted bisnadimides of the present invention, particularly preferred compounds for use as an adhesive or a coating material are N,N'-o-xylylene-bis (allyl-bicyclo[ 2.2.1]hept-5-ene-2,3-dicarboximide), N,N'-m-xylylene-bis-(allyl-bicyclo[ 2.2.1]hept-5-ene-2,3-dicarboximide), N,N'-p-xylylene-bis(allyl-bicyclo[ 2.2.1]hept-5-ene-2,3-dicarboximide[, and N,N'-m-xylylene-bis(methallyl-bicyclo[ 2.2.1]hept-5-ene-2,3-dicarboximide).

The adhesive comprising the alkenyl-substituted bisnadimide of the present invention as a curing component exhibits excellent heat resistance at a high temperature of 250° C. or higher for a long period of time, and the coating material comprising the alkenyl-substituted bisnadimide of the present invention as a curing component exhibits excellent boiling water resistance.

When the alkenyl-substituted bisnadimide of the present invention is used as an adhesive or a coating material, absence of a curing catalyst is rather preferred in view of adhesiveness to substrates or fitness to the surface to be coated. Of course, a curing catalyst may be present depending on the requirements. The use of a solvent is not always essential, because said alkenyl-substituted bisnadimides have a low softening point. When a solvent is used, most common solvents, such as benzene, toluene, xylene, methyl ethyl ketone, acetone, diethyl ether, can be acceptable. Further, methylpyrrolidon, dimethylsulfoxide, and the like, can be also used. These solvents can be used either singly or in combination of two or more. Regarding the concentration of alkenyl-substituted bisnadimides in the solution when a solvent is used, an extremely dilute solution is used for the purpose of forming thin films. On the other hand, a high concentration solution is used for adhesive. Usually, a concentration in the range of 5–70% by weight is applicable.

There are no limitations as to the manner in which the adhesives or the coating materials of the present invention are applied. General application means, such as brushes, applicators, rollers, spatulas and sprays can be used.

In curing the alkenyl-substituted bisnadimide of the present invention, when a solvent is used, it is first removed after the application of the adhesives or the coating materials, then polymerization-curing is carried out at 80°–400° C., preferably 8°–300° C., for 0.001–10 hours, preferably 0.005–5 hours. In order to complete the curing reaction at a relatively low temperature in a relatively short period of time, the use of the above-mentioned curing catalyst is desirable.

If necessary, adhered products or coated films thus obtained may be treated with heat at 150°–350° C. for 0.5–30 hours.

Carbon black or commonly used pigments such as titanium oxide may be added to the coating material of the present invention.

The adhesive or the coating material of the present invention can be used for adhering or coating metals, such as steel, aluminium, or copper; glass, resin, cement, ceramics, and the like. It is especially effective when used as an adhesive requiring heat resistance at a high temperature of 250° C. or higher for a long period of time, or as a coating material requiring resistance to boiling water for a long period of time, such as a coating material to be applied to surfaces exposed-to boiling water or high temperature steam, such as hot water boilers, boiling water tanks, and hot water pipes.

When the alkenyl-substituted bisnadimide of the present invention is used for the applications other than adhesives or coating materials, for example, as a material for molding articles, it is melted together with a curing catalyst, as needed, molded by cast molding, injection molding, or press molding, and cured at 80°–280° C., preferably at 120°–260° C., for 0.01–8 hours, preferably 0.05–5 hours.

When the alkenyl-substituted bisnadimide of the present invention is used as a matrix resin, various kinds of fillers, such as glass fibers, carbon fibers, metal fibers, ceramic fibers, calcium phosphate, calcium carbonate, magnesium carbonate, aluminum hydroxide, magnesium hydroxide, antimony oxide, gypsum, silica, alumina, clay, talc, quarts powders, and carbon black, in an amount of 10–500 parts by weight, are added to and mixed with 100 parts by weight of the alkenyl-substituted bisnadimide to obtain a composite material.

The present invention is hereinafter illustrated by way of examples which shall not be construed as limiting the present invention.

EXAMPLE 1

To a 500 ml flask replaced with nitrogen 154.3 g (0.756 mol) of allyl-bicyclo [2.2.1]hept-5-ene-2,3-dicarboxylic acid anhydride and 200 ml of xylene were charged. To the mixture was added 50 g (0.37 mol) of p-xylylenediamine over 30 minutes with heating and stirring while refluxing xylene. The reaction was continued for 4 hours while separating and removing water produced by the reaction by a water separator. A trace amount of solid residue was separated by filtration and the solvent, xylene, was removed by distillation. The content of time flask was treated with heat at 200° C. under reduced pressure of 1 Torr for 1.5 hours while stirring, thus obtaining 183.6 g [yield based on amine (hereinafter the same):97%] of the target N,N'-p-xylylene-bis(allyl-bicyclo[ 2.2.1]hept-5-ene-2,3-dicarboximide), of which the chemical structure is shown by the following formula [5]. This compound is hereinafter abbreviated to BANI-pX.

[5]

Figure 1:
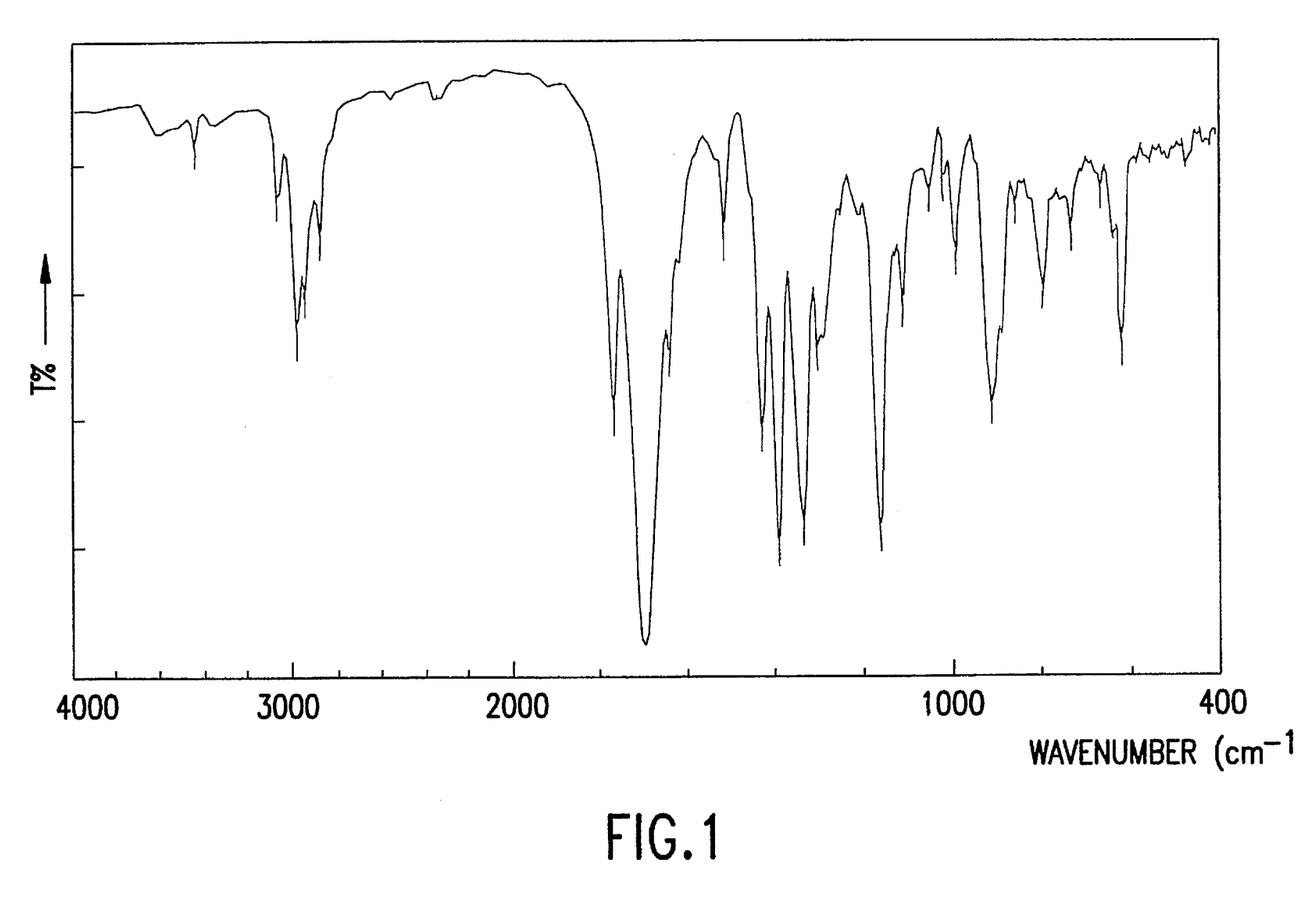
FIG. 1 is an IR spectrum of N,N'-p-xylylene-bis (allyl-bicyclo [2.2.1]hept-5-ene-2,3-dicarboximide) (hereinafter referred to BANI-pX) obtained in Example 1.
Figure 2:
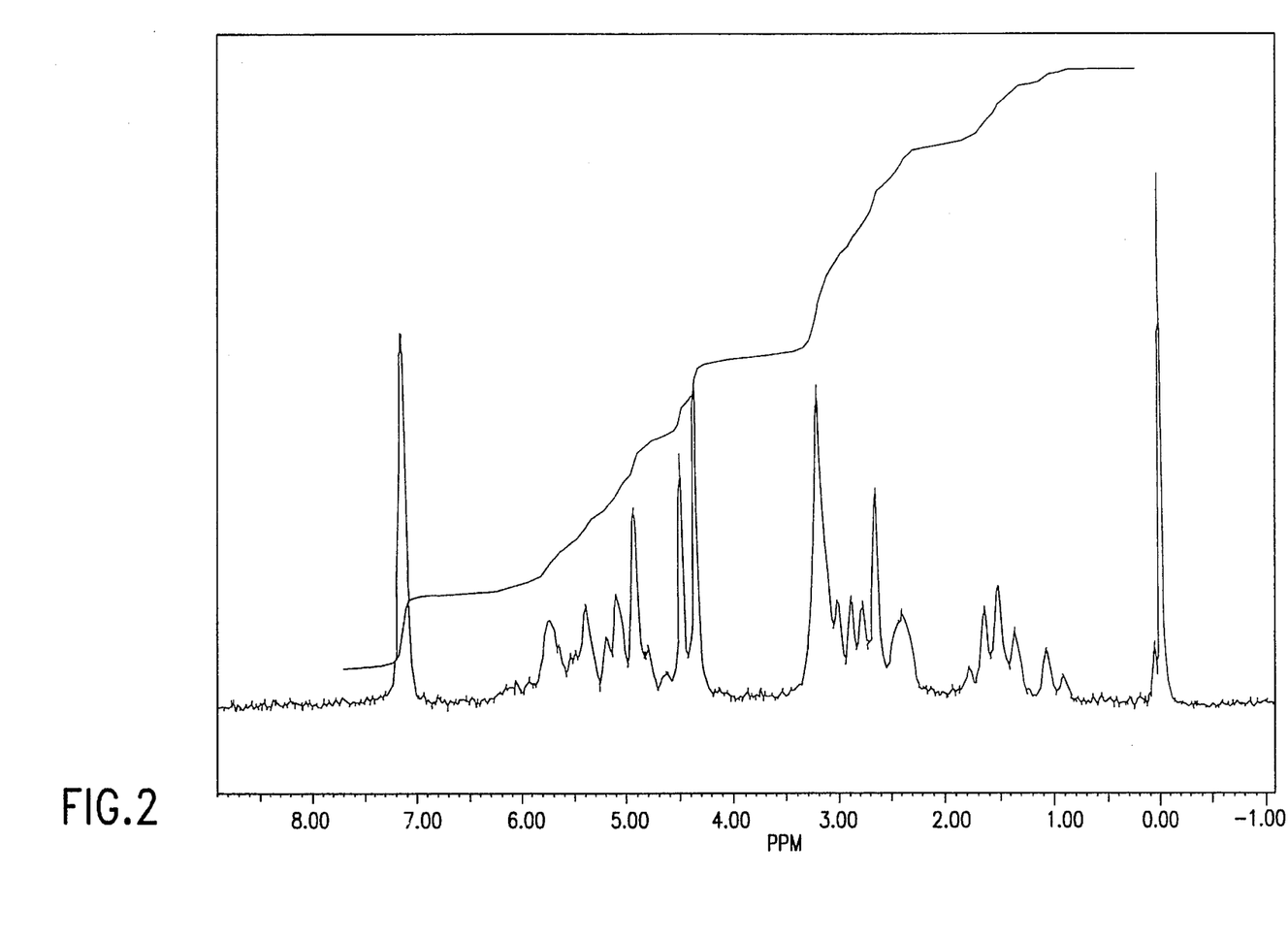
FIG. 2 is a $^1$H-NMR spectrum of BANI-pX obtained in Example 1.

The IR spectrum and $^1$H-NMR spectrum (60 MHz) of BANI-pX are shown in FIGS. 1 and 2, respectively.

In the IR spectrum, the following absorptions were identified.

Alkene C—H stretching: 3074, 2978 cm$^{-1}$
Aromatic C—H stretching: 2978 cm$^{-1}$
Alkane C—H stretching: 2943 cm$^{-1}$
Imide C=O stretching: 1769, 1699 cm$^{-1}$
C=C stretching: 1641 cm$^{-1}$
—CH$_2$—N methylene scissors: 1429 cm$^{-1}$
Imide C—N stretching: 1393 cm$^{-1}$ In the $^1$H-NMR spectrum, the following peaks were identified.

a–d protons (4H): 7.0–7.3 ppm
e–g protons (8H): 4.7–5.9 ppm
h protons (4H): 4.2–4.7 ppm
i–m protons (12H): 2.2–3.4 ppm
n protons (4H): 0.8–2.0 ppm The elementary analysis revealed the results of C:75.0 wt. %, H:6.1 wt. %, and N:5.5 wt. % (calculated values, C:75.57 wt. %, H:6.34 wt. %, and N:5.51 wt. %).

The properties of BANI-pX were as follows:

(1) Pale yellow solid with a melting point, measured by a micro melting point apparatus, of about 55° C.

(2) Easily soluble in N,N-dimethylformamide, methyl ethyl ketone, tetrahydrofuran, ethyl acetate, toluene, and the like, and insoluble in hexane and methanol.

EXAMPLE 2

To a 1000 ml flask replaced with nitrogen 257.4 g (1.26 mol) of allyl-bicyclo[2.2.1]hept-5-ene-2,3-dicarboxylic acid anhydride and 300 ml of xylene were charged. To the mixture was added 81.4 g (0.60 mol) of m-xylylenediamine over 1.5 hours with heating and stirring while refluxing xylene. The reaction was continued for 3 hours while separating and removing water produced by the reaction by a water separator, and then the solvent, xylene, was removed by distillation. Thereafter, the content of the flask was treated with heat at 200° C. under reduced pressure of 1 Torr for 1 hour while stirring, thus obtaining 301.8 g (yield: 99%) of the target N,N'-m-xylylene-bis(allyl-bicyclo [2.2.1]hept-5-ene-2,3-dicarboximide), of which the chemical structure is shown by the following formula [6]. This compound is hereinafter abbreviated to BANI-mX.

[6]

Figure 3:
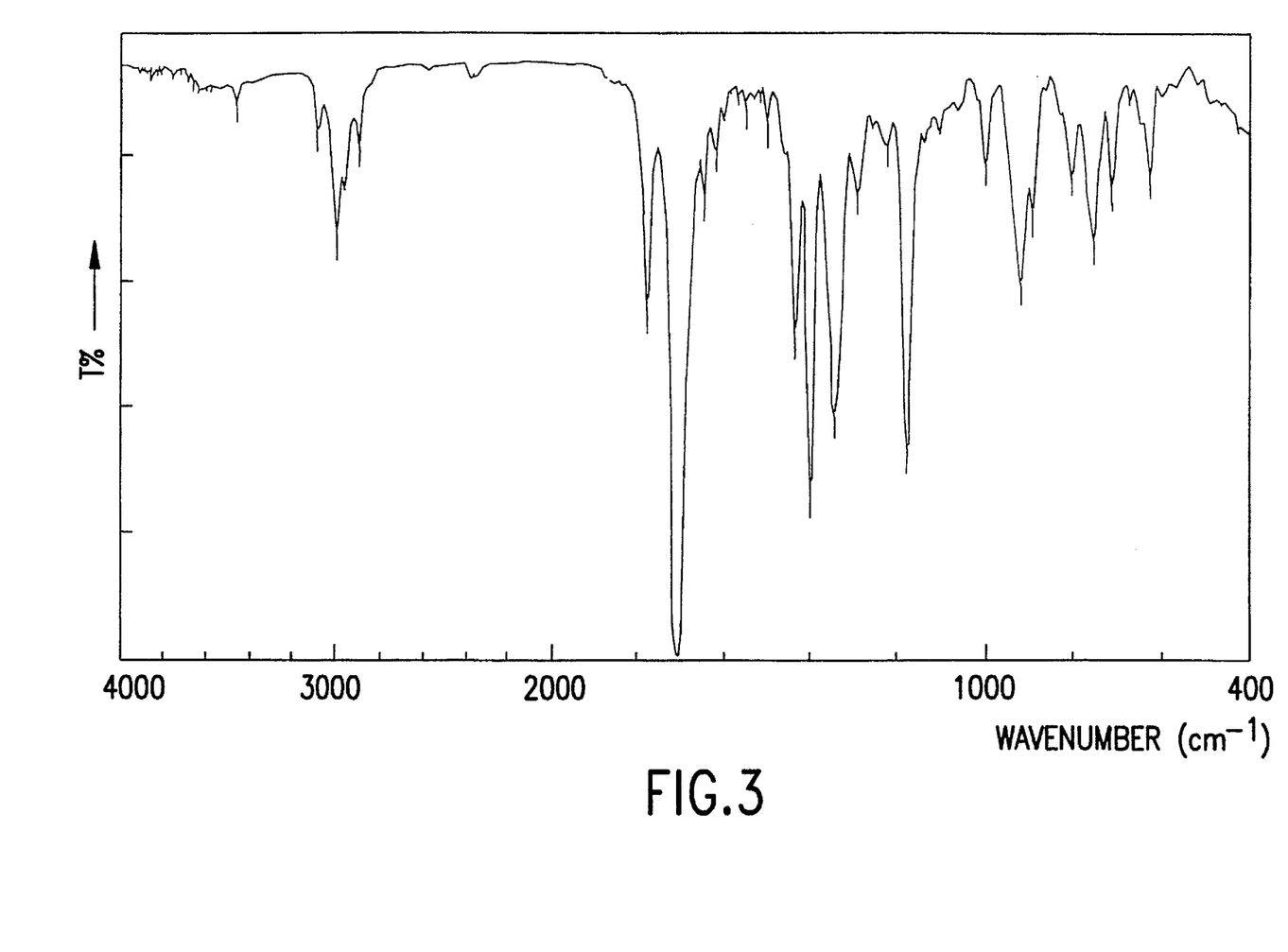
FIG. 3 is an IR spectrum of N,N'-m-xylylene-bis (allyl-bicyclo [2.2.1]hept-5-ene-2,3-dicarboximide) (hereinafter referred to BANI-mX) obtained in Example 2.
Figure 4:
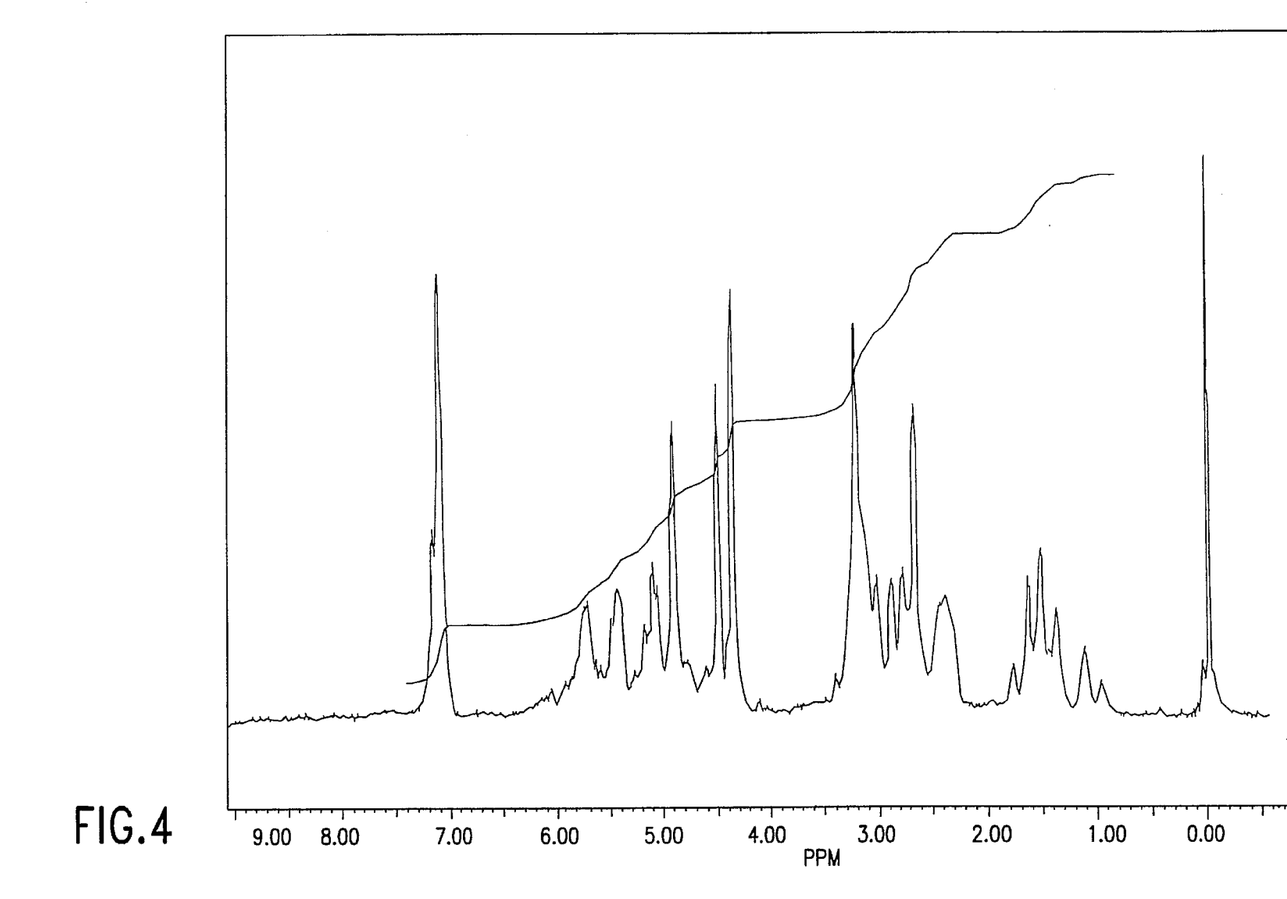
FIG. 4 is a $^1$H-NMR spectrum of BANI-mX obtained in Example 2.

The IR spectrum and $^1$-NMR spectrum (60 MHz) of BANI-mX are shown in FIGS. 3 and 4, respectively.

In the IR spectrum, the following absorptions were identified.

Alkene C—H stretching: 3075, 2979 cm$^{-1}$
Aromatic C—H stretching: 2979 cm$^{-1}$
Alkane C—H stretching: 2943 cm$^{-1}$
Imide C=O stretching: 1769, 1701 cm$^{-1}$
C=C stretching: 1641 cm$^{-1}$
—CH$_2$—N methylene scissors: 1428 cm$^{-1}$ Imide C—N stretching: 1394 cm$^{-1}$ In the $^1$H-NMR spectrum, the following peaks were identified.

a–d protons (4H): 7.0–7.3 ppm e–g protons (8H): 4.7–6.0 ppm h protons (4H): 4.2–4.7 ppm i–m protons (12H): 2.2–3.4 ppm n protons (4H): 0.8–1.9 ppm The elementary analysis revealed the results of C:75.3 wt. %, H:6.4 wt. %, and N:5.4 wt. % (calculated values, C:75.57 wt. %, H:6.34 wt. %, and N:5.51 wt. %).

The properties of BANI-mX were as follows:

(1) Pale yellow solid with a melting point, measured by a micro melting point apparatus, of about 42° C.

(2) Specific Gravity (23° C./23° C.): 1.213

(3) Viscosity: 4.0×10$^4$ mPa.s (80° C.) 3.5×10$^3$ mPa.s (100° C.)

(4) Easily soluble in N,N-dimethylformamide, methyl ethyl ketone, tetrahydrofuran, ethyl acetate, toluene, and the like, partly soluble in methanol and insoluble in hexane.

EXAMPLE 3

To a 300 ml flask replaced with nitrogen 61.7 g (0.302 mol) of allyl-bicyclo[2.2.1]hept-5-ene-2,3-dicarboxylic acid anhydride and 100 ml of xylene were charged. To the mixture was added 20 g (0.15 mol) of 2-(4-aminophenyl-)ethylamine over 30 minutes with heating and stirring while refluxing xylene. The reaction was continued for 4 hours while separating and removing water produced by the reaction by a water separator. A trace amount of solid residue was separated by filtration and the solvent, xylene, was removed by distillation. Then, the content of the flask was treated with heat at 200° C. under reduced pressure of 1 Torr for 1 hour while stirring, thus obtaining 70.7 g (yield:88%) of the target N,N'-(p-phenylene).ethylene-bis(allyl-bicyclo[2.2.1]hept-5-ene- 2,3-dicarboximide), of which the chemical structure is shown by the following formula [7]. This compound is hereinafter abbreviated to BANI-PE.

Figure 5:
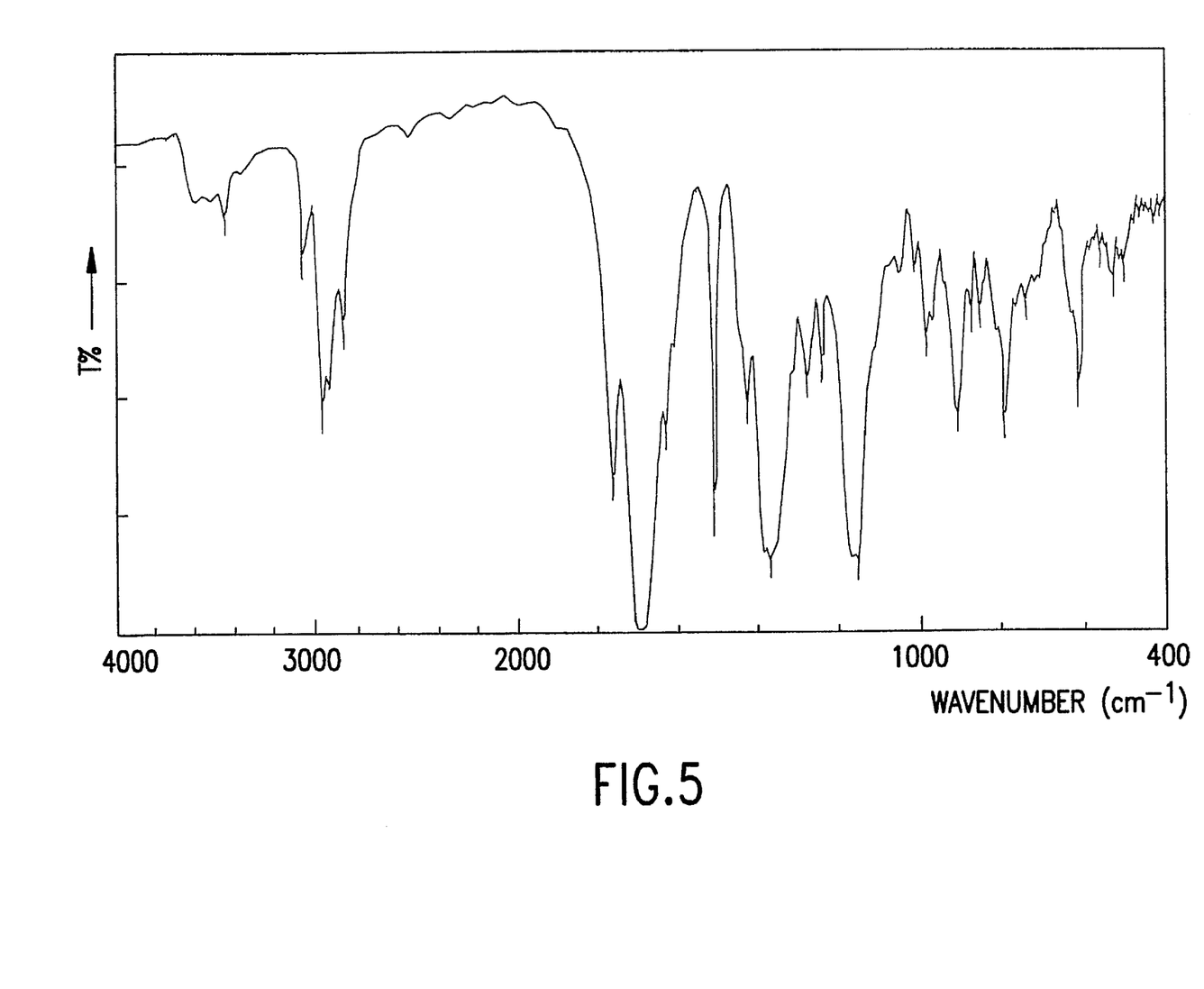
FIG. 5 is an IR spectrum of N,N'-(p-phenylene).ethylene-bis(allyl-bicyclo[ 2.2.1]hept-5-ene-2,3-dicarboximide) (hereinafter referred to BANI-PE) obtained in Example 3.

Alkene C—H stretching: 3075, 2977 cm$^{-1}$

Aromatic C—H stretching: 2977 cm$^{-1}$

Alkane C—H stretching: 2943 cm$^{-1}$

Imide C=O stretching: 1772, 1709 cm$^{-1}$

C=C stretching: 1641 cm$^{-1}$

—CH$_2$—N methylene scissors: 1434 cm$^{-1}$

Imide C—N stretching: 1394 cm$^{-1}$

Figure 6:
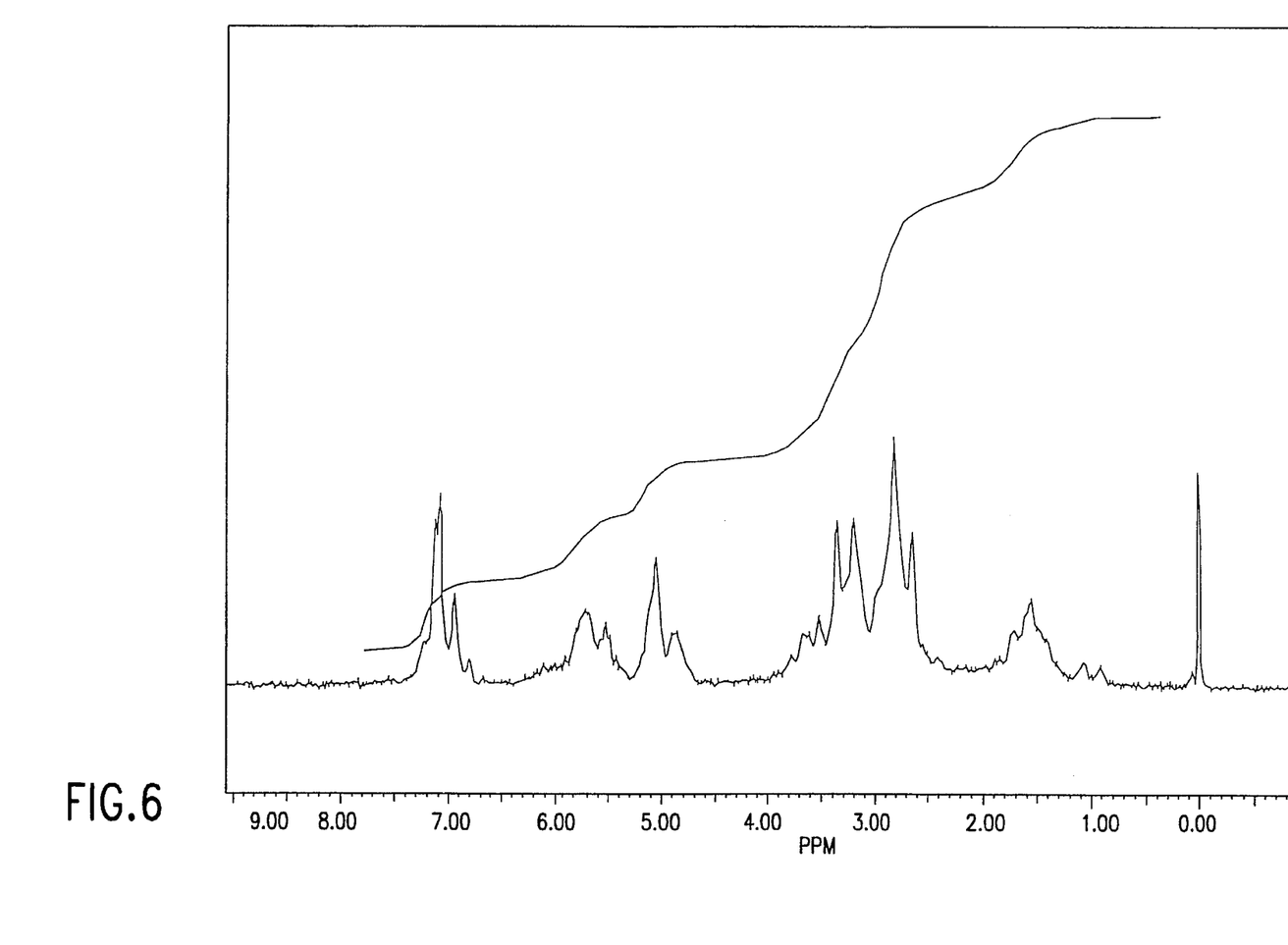
FIG. 6 is a $^1$H-NMR spectrum of BANI-PE obtained in Example 3.

In the $^1$H-NMR spectrum, the following peaks were identified.

a–d protons (4H): 6.8–7.4 ppm e–g protons (8H): 4.7–6.0 ppm h–n protons (16H): 2.5–3.9 ppm o protons (4H): 0.8–1.9 ppm The elementary analysis revealed the results of C:75.8 wt. %, H:6.2 wt. %, and N:5.4 wt. % (calculated values, C:75.57 wt. %, H:6.34 wt. %, and N:5.51 wt. %).

The properties of BANI-PE were as follows:

(1) Amber solid with a melting point, measured by a micro melting point apparatus, of about 83° C.

(2) Easily soluble in N,N-dimethylformamide, methyl ethyl ketone, tetrahydrofuran, ethyl acetate, toluene, and the like, and insoluble in hexane and methanol.

EXAMPLE 4

To a 1000 ml flask replaced with nitrogen 172.0 g (0.843 mol) of allyl-bicyclo[2.2.1]hept-5-ene-2,3-dicarboxylic acid anhydride and 200 ml of xylene were charged. To the mixture was added 50 g (0.41 mol) of 2-aminobenzylamine over 30 minutes with heating and stirring while refluxing xylene. The reaction was continued for 4 hours while separating and removing water produced by the reaction by a water separator. Then, the solvent, xylene, was removed by distillation. The content of the flask was treated with heat at 200° C. under reduced pressure of 1 Torr for 1 hour while stirring, thus obtaining 156.7 g (yield: 77%) of the target N,N'-(o-phenylene).methylene-bis(allyl-bicyclo[ 2.2.1] hept-5-ene-2,3-dicarboximide), of which the chemical structure is shown by the following formula [8]. This compound

[7]

The IR spectrum and $^1$H-NMR spectrum (60 MHz) of BANI-PE are shown in FIGS. 5 and 6, respectively.

In the IR spectrum, the following absorptions were identified.

is hereinafter abbreviated to BANI-PM.

[8]

Figure 7:
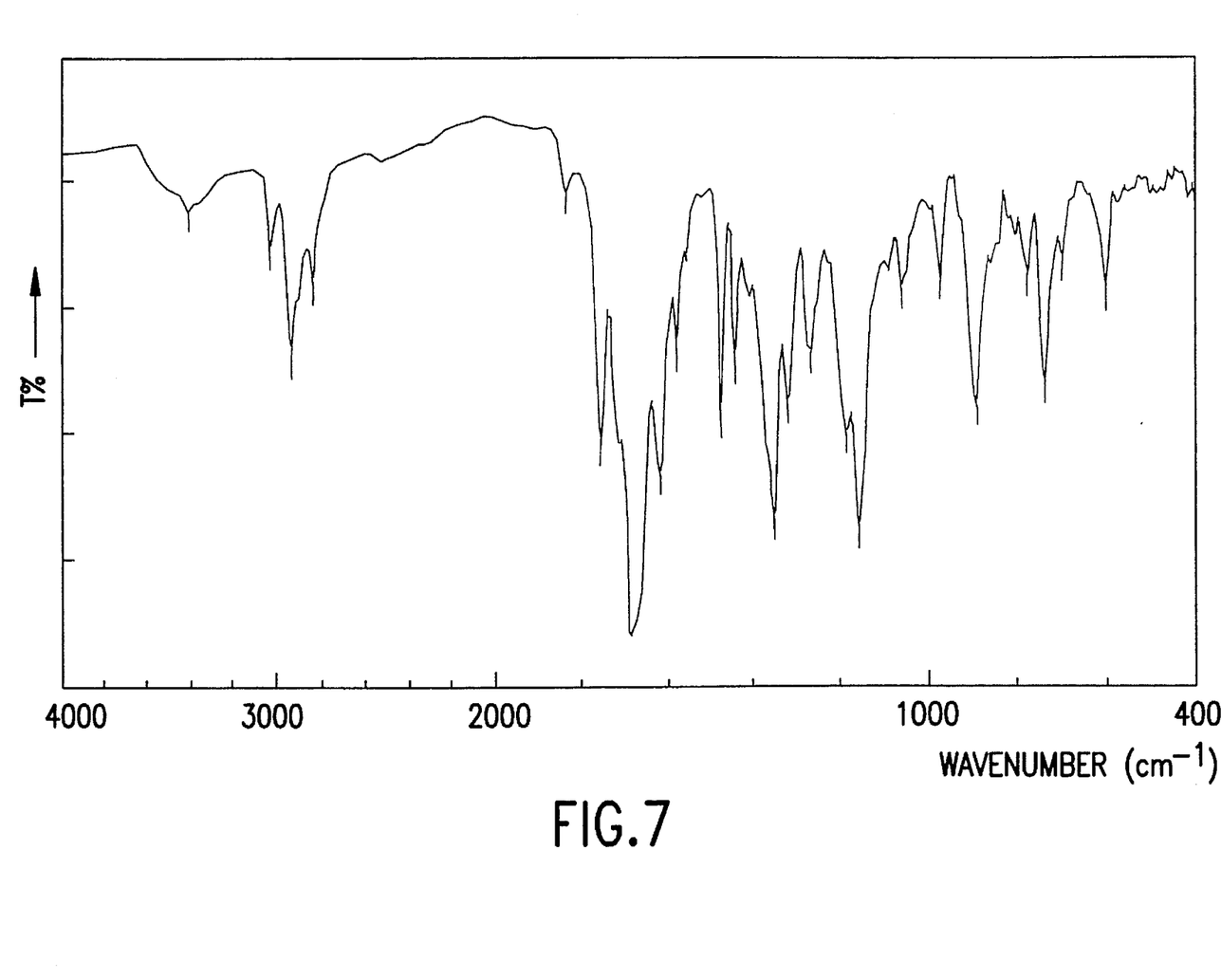
FIG. 7 is an IR spectrum of N,N'-(o-phenylene).methylene-bis(allyl-bicyclo[ 2.2.1]hept-5-ene-2,3-dicarboximide) (hereinafter referred to BANI-PM) obtained in Example 4.
Figure 8:
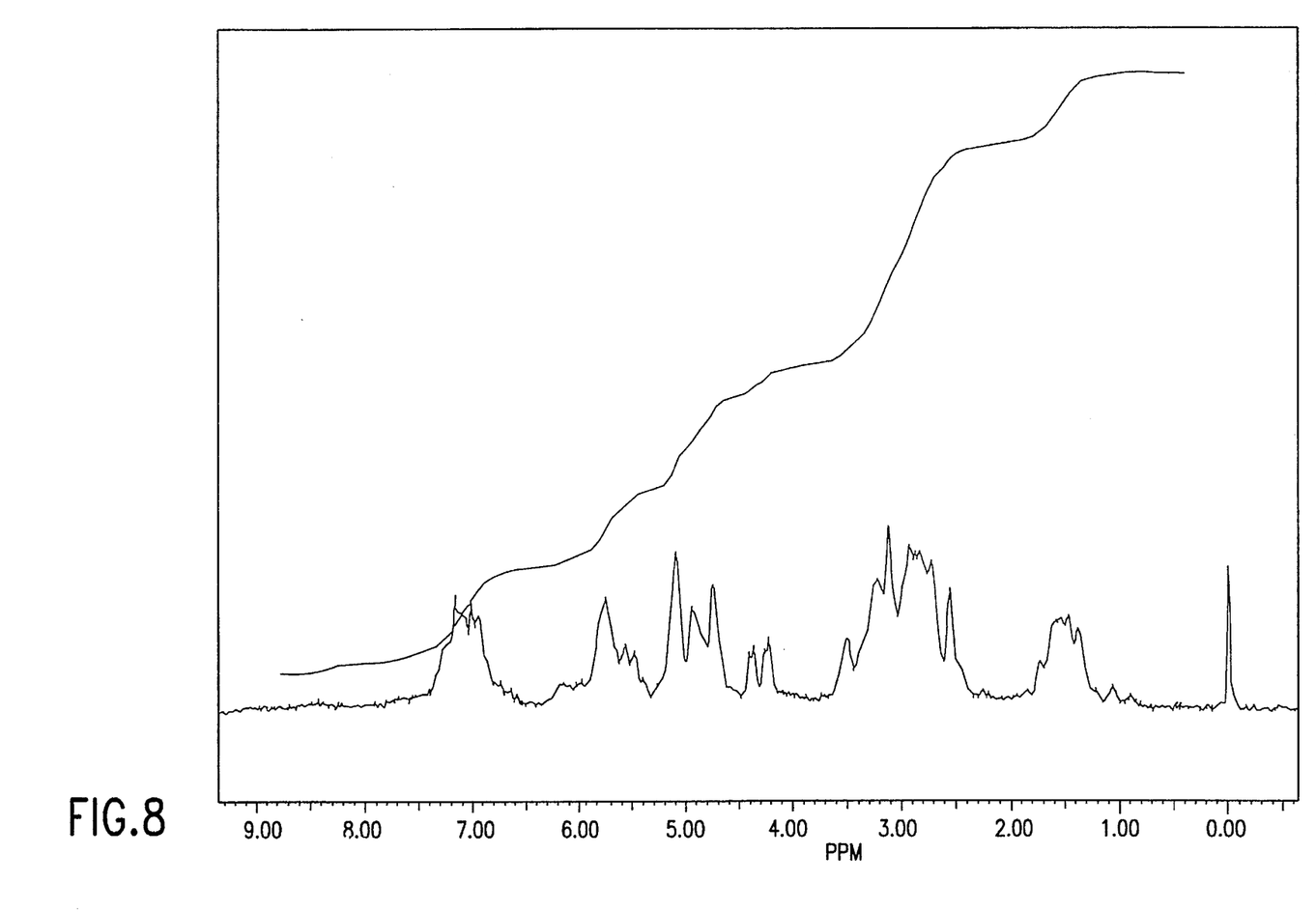
FIG. 8 is a $^1$H-NMR spectrum of BANI-PM obtained in Example 4.

The IR spectrum and $^1$H-NMR spectrum (60 MHz) of BANI-PM are shown in FIGS. 7 and 8, respectively.

In the IR spectrum, the following absorptions were identified.

Alkene C—H stretching: 3074, 2977 cm$^{-1}$

Aromatic C—H stretching: 2977 cm$^{-1}$

Alkane C—H stretching: 2943 cm$^{-1}$

Imide C=O stretching: 1780, 1709 cm$^{-1}$

C=C stretching: 1642 cm$^{-1}$

—CH$_2$—N methylene scissors: 1434 cm$^{-1}$

Imide C—N stretching: 1394 cm$^{-1}$

In the $^1$H-NMR spectrum, the following peaks were identified.

a–d protons (4H): 6.5–7.4 ppm e–g protons (8H): 4.5–5.9 ppm h protons (2H): 4.1–4.5 ppm i–m protons (12H): 2.3–3.6 ppm n protons (4H): 0.8–1.9 ppm The elementary analysis revealed the results of C:75.0 wt. %, H:6.1 wt. %, and N:5.5 wt. % (calculated values, C:75.28 wt. %, H:6.11 wt. %, and N:5.66 wt. %).

The properties of BANI-PM were as follows:

(1) Black solid with a melting point, measured by a micro melting point apparatus, of about 116° C.

(2) Easily soluble in N,N-dimethylformamide, methyl ethyl ketone, tetrahydrofuran, ethyl acetate, toluene, and the like, partly soluble in methanol, and insoluble in hexane.

EXAMPLES 5–11

5 g of powder of BANI-mX prepared in Example 2 was blended homogeneously with 0.05 g of various kinds of cationic catalysts shown in Table 1. A portion of each blend was placed on a hot plate exposed to air at a temperature of 200° C. A period of time required for each sample to gel (gelling time) was measured while agitating the mixture at this temperature. The results are shown in Table 1.

TABLE 1

|  | Cationic Catalysts | Gelling time (min:sec) |
| --- | --- | --- |
| Example 5 | Aluminum chloride | 11:00 |
| Example 6 | Ferric chloride | 12:00 |
| Example 7 | Nickel chloride | 15:30 |
| Example 8 | Methyl p-toluenesulfonate | 10:00 |
| Example 9 | ANI-BsE | 12:00 |
| Example 10 | Aniline sulfate | 10:30 |
| Example 11 | β-naphthalenesulfonic acid | 8:00 |

ANI-BsE: N-(2-benzenesulfonylhydroxyethyl)-allyl-bicyclo[2.2.1]hept-5-ene-2,3-dicarboximide

EXAMPLES 12–15

5 g of powder of BANI-mX prepared in Example 2 was blended homogeneously with 0.05 g of various kinds of cationic catalysts shown in Table 2. A portion of each blend was placed on a hot plate exposed to air at a temperature of 180° C. A period of time required for each sample to gel (gelling time) was measured while agitating the mixture at this temperature. The results are shown in Table 2.

TABLE 2

| Cationic Catalysts | Gelling time (min:sec) |
| --- | --- |
| Example 12 p-Toluenesulfonic acid | 20:00 |
| Example 13 Sulfuric acid-pyridine complex | 20:00 |
| Example 14 Pyridinium p-toluenesulfollate | 20:00 |
| Example 15 Dimethyl sulfate | 12:00 |

EXAMPLES 16–18

5 g of powder of BANI-mX prepared in Example 2 was blended homogeneously with 0.05 g of various kinds of onium salt catalysts shown in Table 3. A portion of each blend was placed on a hot plate exposed to air at a temperature of 200° C. A period of time required for each sample to gel (gelling time) was measured while agitating the mixture at this temperature. The results are shown in Table 3.

TABLE 3

| | Onium Salt | Gelling time (min:sec) |
| --- | --- | --- |
| Example 16 | Diphenyliodonium perchlorate | 4:00 |
| Example 17 | Diphenyliodonium hexafluorophosphate | 15:00 |
| Example 18 | Diphenyliodonium tetrafluoroborate | 17:00 |

EXAMPLES 19–22

5 g of powder of BANI-mX prepared in Example 2 was blended homogeneously with 0.05 g of various kinds of the organic compounds of transition elements shown in Table 4. A portion of each blend was placed on a hot plate exposed to air at a temperature of 200° C. A period of time required for each sample to gel (gelling time) was measured while agitating the mixture at this temperature. The results are shown in Table 4.

TABLE 4

| | Organic Compound of Transition Element | Gelling time (min:sec) |
| --- | --- | --- |
| Example 19 | Ferric stearate | 10:00 |
| Example 20 | Manganese (III) acetylacetonate | 12:00 |
| Example 21 | Acetylferrocene | 10:30 |
| Example 22 | Cerium (III) acetylacetonate | 8:00 |

EXAMPLES 23–24

5 g of powder of BANI-mX prepared in Example 2 was blended homogeneously with 0.05 g of two kinds of organic peroxides shown in Table 5. A portion of each blend was placed on a hot plate exposed to air at a temperature of 200° C. A period of time required for each sample to gel (gelling time) was measured while agitating the mixture at this temperature. The results are shown in Table 5.

TABLE 5

| | Organic Peroxide | Gelling time (min:sec) |
| --- | --- | --- |
| Example 23 | Dicumyl peroxide | 18:00 |

TABLE 5-continued

| | Organic Peroxide | Gelling time (min:sec) |
|---|---|---|
| Example 24 | Cumene hydroperoxide | 20:00 |

EXAMPLES 25–27

5 g of powder of BANI-mX prepared in Example 2 were blended homogeneously with 0.025 g of dicumyl peroxide and 0.025 g of various kinds of the organic compounds of transition elemens shown in Table 6. A portion of each blend was placed on a hot plate exposed to air at a temperature of 200° C. A period of time required for each sample to gel (gelling time) was measured while agitating the mixture at this temperature. The results are shown in Table 6.

TABLE 6

| | Organic Compound of Transition Element | Gelling time (min:sec) |
|---|---|---|
| Example 25 | Manganese (III) Acetylacetonate | 8:30 |
| Example 26 | Nickel (II) Acetylacetonate | 13:00 |
| Example 27 | Vanadium (III) Acetylacetonate | 12:00 |

EXAMPLE 28

BANI-pX prepared in Example 1 was melted at 200° C. for 30 minutes under vacuum to deaerate, and charged into a metal mold and heated at 250° C. for 24 hours under atmospheric pressure to obtain a cured product with the following characteristics.

Glass transition temperature (TMA method, Tg): 308° C.

Coefficient of linear thermal expansion (1/° C.) (JIS-K7197) (Room temperature to Tg): $5.19 \times 10^{-5}$ 5% weight loss temperature (in nitrogen, TGA method): 444° C.

Flexural strength (JIS-K7203): 10.8 Kg/mm$^2$

Flexural modulus (JIS-K7203): 355 Kg/mm$^2$

EXAMPLE 29

BANI-mX prepared in Example 2 was melted at 200° C. for 30 minutes under vacuum to deaerate, and charged into a metal mold and heated at 260° C. for 20 hours under atmospheric pressure to obtain a cured product with the following characteristics.

Specific Gravity (JIS-K7112) (23° C./23° C.): 1.222

Glass transition temperature (TMA method, Tg): 308° C.

Coefficient of linear thermal expansion (1/° C.) (Room temperature to Tg): $4.83 \times 10^{-5}$ Distortion temperature at load (high load method) (JIS-K7207 A method): 311° C.

5% weight loss temperature (in nitrogen, TGA method): 437° C.

Flexural strength: 14.3 Kg/mm$^2$

Flexural modulus: 391 Kg/mm$^2$

Tensile strength (JIS-K7113): 7.7 Kg/mm$^2$

Tensile modulus (JIS-K7113): 370 Kg/mm$^2$

Compressive strength (JIS-K7208): 18.2 Kg/mm$^2$

Izod impact value (JIS-K7110): 1.8 kj/m$^2$

Rockwell hardness (JIS-K7202): 127 HRM

Volume resistivity (JIS-K6911) (500 V D.C 1 min): $9.41 \times 10^{16} \Omega \cdot cm$ Surface resistivity (JIS-K6911) (500 V D.C 1 min): $2.81 \times 10^{16} \Omega$ Dielectric constant ($\epsilon$) (JIS-K6911) (1 MHz): 3.09

Dielectric loss (tan$\delta$) (JIS-K6911) (1 MHz): $1.11 \times 10^{-2}$

EXAMPLE 30

BANI-mX prepared in Example 2 was melted at 170° C. and 1 wt. % of diphenyliodonium hexafluorophosphate was added thereto and dissolved therein. Thereafter, time molten material was deaerated for 2 minutes and charged into a metal mold and heated at 200° C. for 10 hours under atmospheric pressure to obtain a cured product with the following characteristics.

Glass transition temperature (TMA method, Tg): 221° C.

Flexural strength: 16.0 Kg/mm$^2$

Flexural modulus: 380 Kg/mm$^2$

EXAMPLE 31

A curing test was conducted in the same manner as in Example 30 except that 1 wt. % of pyridinium p-toluenesulfonate was used instead of 1 wt. % of diphenyliodonium hexafluorophosphate used in Example 30. A cured product having the following characteristics was obtained.

Glass transition temperature (TMA method, Tg): 216° C.

Flexural strength: 13.5 Kg/mm$^2$

Flexural modulus: 403 Kg/mm$^2$

EXAMPLE 32

BANI-PE prepared in Example 3 was melted at 200° C. for 30 minutes under vacuum to deaerate, and charged into a metal mold and heated at 250° C. for 24 hours under atmospheric pressure to obtain a cured product with the following characteristics.

Glass transition temperature (TMA method, Tg): 306° C.

Coefficient of linear thermal expansion (1/° C.) (Room temperature to Tg): $5.23 \times 10^{-5}$ 5% weight loss temperature (in nitrogen, TGA method): 444° C.

Flexural strength: 11.1 Kg/mm$^2$

Flexural modulus: 340 Kg/mm$^2$

EXAMPLE 33

BANI-PM prepared in Example 4 was melted at 200° C. for 30 minutes under vacuum to deaerate, and charged into a metal mold and heated at 250° C., for 24 hours under atmospheric pressure. A cured product having 5% weight loss temperature (in nitrogen, TGA method) of 403° C. was obtained.

Comparative Example 1

Bis[4-(allyl-bicyclo [2.2.1]hept-5-ene-2,3-dicarboximide)phenyl] methane (hereinafter referred to BANI-M) was prepared according to the process described in U.S. Pat. No. 4,515,962. BANI-M thus obtained was cured in the same manner as in Example 29 to obtain a cured product with the following characteristics.

Specific Gravity (23° C./23° C.): 1.219

Glass transition temperature (TMA method, Tg): 336° C.

Coefficient of linear thermal expansion (1/° C.) (Room temperature to Tg): $5.15 \times 10^{-5}$ Distortion temperature at load (high load method): 348° C.

5% weight loss temperature (in nitrogen, TGA method): 445° C.

Flexural strength: 13.8 Kg/mm$^2$

Flexural modulus: 336 Kg/mm$^2$

Tensile strength: 4.0 Kg/mm$^2$

Tensile modulus: 296 Kg/mm$^2$

Compressive strength: 19.4 Kg/mm$^2$

Izod impact value: 1.1 kj/m$^2$

Rockwell hardness: 128 HRM

Volume resistivity (500 V D.C 1 min): $1.74 \times 10^{17}$ Ω·cm

Surface resistivity (500V D.C 1 min): $1.87 \times 10^{17}$ Ω

Dielectric constant (ε) (1 MHz): 3.18

Dielectric loss (tanδ) (1 MHz): $1.20 \times 10^{-2}$

Comparative Example 2

N,N'-hexamethylene-bis(allyl-bicyclo[2.2.1]hept-5-ene-2,3-dicarboximide) (hereinafter referred to BANI-H) was prepared according to the process described in U.S. Pat. No. 4,515,962. BANI-H thus obtained was cured in the same manner as in Example 29 to obtain a cured product with the following characteristics.

Specific Gravity (23° C./23° C.): 1.196

Glass transition temperature (TMA method, Tg): 309° C.

Coefficient of linear thermal expansion (1/° C.) (Room temperature to Tg): $6.73 \times 10^{-5}$ Distortion temperature at load (high load method): 307° C.

5% weight loss temperature (in nitrogen, TGA method): 438° C.

Flexural strength: 11.6 Kg/mm$^2$

Flexural modulus: 201 Kg/mm$^2$

Tensile strength: 5.5 Kg/mm$^2$

Tensile modulus: 244 Kg/mm$^2$

Compressive strength: 14.2 Kg/mm$^2$

Izod impact value: 1.5 kj/m$^2$

Rockwell hardness: 123 HRM

Volume resistivity (500 V D.C 1 min): $3.22 \times 10^{17}$ Ω·cm

Surface resistivity (500 V D.C 1 min): $>1.00 \times 10^{17}$ Ω

Dielectric constant (ε) (1 MHz): 2.88

Dielectric loss (tanδ) (1 MHz): $1.04 \times 10^{-2}$

EXAMPLES 34–37

Comparative Examples 3–6

Solutions of alkenyl-substituted bisnadimides (30 wt. %) in xylene shown in Table 7 were applied to mild steel plate by spraying and baked at 200° C. for 20 minutes in air. All produced a coated film with a thickness of 10–15 μm exhibiting superior adhesion properties and solvent resistance.

These test specimens were placed in a thermostat at 300° C. for a prescribed period of time and their adhesion properties were examined. The results are shown in Table 7.

TABLE 7

| | | Holding time in the thermostat | |
|---|---|---|---|
| | Sample | 16 hours | 100 hours |
| Example 34 | BANI-PM | ◯ | ◯ |
| Example 35 | BANI-PE | ◯ | ◯ |
| Example 36 | BANI-pX | ◯ | ◯ |
| Example 37 | BANI-mX | ◯ | ◯ |
| C. Example 3 | BANI-H | X | X |
| C. Example 4 | BANI-M | ◯ | X |
| C. Example 5 | BANI-PD | ◯ | X |
| C. Example 6 | BANI-TD | X | X |

C. Example: Comparative Example
Test procedure for determining adhesion property: JIS-K5400 cheker test
◯: 100% retained; Δ: 99–95% retained, i.e., 1–5% damaged; X: less than 95% retained, i.e., more than 5% damaged.
BANI-PM: N,N'-(o-phenylene).methylene-bis(allyl-bicyclo[2.2.1]hept-5-ene-2,3-dicarboximide)
BANI-PE: N,N'-(p-phenylene).ethylene-bis(allyl-bicyclo[2.2.1]hept-5-ene-2,3-dicarboximide)
BANI-pX: N,N'-p-xylylene-bis(allyl-bicyclo[2.2.1]hept-5-ene-2,3-dicarboximide)
BANI-mX: N,N'-m-xylylene-bis(allyl-bicyclo[2.2.1]hept-5-ene-2,3-dicarboximide)
BANI-H: N,N'-hexamethylene-bis(allyl-bicyclo[2.2.1]hept-5-ene-2,3-dicarboximide)
BANI-M: Bis[4-(allyl-bicyclo[2.2.1]hept-5-ene-2,3-dicarboximide)phenyl]methane
BANI-PD: N,N'-m-phenylene-bis(allyl-bicyclo[2.2.1]hept-5-ene-2,3-dicarboximide)
BANI-TD: N,N'-(1-methyl-2,4-phenylene)-bis(allyl-bicyclo[2.2.1]hept-5-ene-2,3-dicarboximide)

EXAMPLES 38–41

Comparative Examples 7–10

Solutions of alkenyl-substituted bisnadimides (30 wt. %) in xylene shown in Table 7 were applied to aluminum plate by spraying and baked at 200° C. for 20 minutes in air. All produced a coated film with a thickness of 10–15 μm exhibiting superior adhesion properties and solvent resistance.

These test specimens were placed in a thermostat at 300° C. for a prescribed period of time and their adhesion properties were examined. The results are shown in Table 8.

TABLE 8

| | | Holding time in the thermostat | |
|---|---|---|---|
| | Sample | 16 hours | 100 hours |
| Example 38 | BANI-PM | ◯ | ◯ |
| Example 39 | BANI-PE | ◯ | ◯ |
| Example 40 | BANI-pX | ◯ | ◯ |
| Example 41 | BANI-mX | ◯ | ◯ |
| C. Example 7 | BANI-H | X | X |
| C. Example 8 | BANI-M | ◯ | X |
| C. Example 9 | BANI-PD | X | X |
| C. Example 10 | BANI-TD | X | X |

Test procedure for determining adhesion property and abbreviations are the same as shown relative to Table 7.

EXAMPLE 42

A 50 wt. % methyl ethyl ketone solution of BANI-mX prepared in Example 2 was applied to two mild steel plates (10×2.5×0.2 cm). After drying at 160° C. for 20 minutes, the two plates were put together, with the coated surfaces vis-a-vis facing, fixed with a clip, and the clipped plates were cured by heating at 250° C. for 3 hours. The test specimens thus obtained were left in an air-circulation type thermostat at 250° C. for a prescribed period of time, i.e., 0 day, 5 days, 10 days, 20 days or 30 days, and a tensile-shearing test (JIS-K6850) was carried out at room temperature and at 250° C. The results are shown in Table 9.

Comparative Example 11

A similar test was carried out in the same manner as in Example 42 except that BANI-H was used instead of BANI-mX used in Example 42. The specimens thus obtained were subjected to tensile-shearing test in the same manner as in Example 42. The results are shown in Table 9.

Comparative Example 12

A similar test was carried out in the same manner as in Example 42 except that BANI-M was used instead of BANI-mX used in Example 42. The specimens thus obtained were subjected to tensile-shearing test in the same manner as in Example 42. The results are shown in Table 9.

Comparative Example 13

A similar test was carried out in the same manner as in Example 42 except that commercially available thermosetting polyimide (BT resin, tradename; Mitsubishi Gas Chemical Company, Inc.) was used instead of BANI-mX used in Example 42. The specimens thus obtained were subjected to tensile-shearing test in the same manner as in Example 42. The results are shown in Table 9.

TABLE 9

| | Adhesion strength obtained by tensile-shearing test (Kg/cm$^2$) | | | |
|---|---|---|---|---|
| | Ex. 42 | C. Ex. 11 | C. Ex. 12 | C. Ex. 13 |
| Initial value | | | | |
| At room temperature | 202 | 186 | 166 | 240 |
| At 250° C. | 157 | 108 | 97 | 150 |
| After 5 days | | | | |
| At room temperature | 185 | 176 | 102 | 219 |
| At 250° C. | 105 | 85 | 67 | 135 |
| After 10 days | | | | |
| At room temperature | 164 | 160 | 76 | 68 |
| At 250° C. | 95 | 87 | 27 | 22 |
| After 20 days | | | | |
| At room temperature | 167 | 159 | 41 | 20 |
| At 250° C. | 103 | 79 | 12 | — |
| After 30 days | | | | |
| At room temperature | 130 | 125 | 41 | — |
| At 250° C. | 100 | 60 | 10 | — |

Ex.: Example;
C. Ex.: Comparative Example;
—: Not measured

EXAMPLE 43

A solution prepared by dissolving 30 g of BANI-mX and 5 g of carbon black in 70 g of toluene and stirring the mixture at room temperature for 30 minutes was applied to a mild steel plate (15×7×0.1 cm). After drying at 130° for 60 minutes, BANI-mX was cured at 180° C. for 20 minutes to obtain a boiling water resistant test specimen with a coated film thickness of 15 μm. The test specimen was dipped in a boiling water at 100° C. in a thermostat for 100 hours, whereupon it was taken out from the thermostat and allowed to cool to room temperature. A cellophane tape was evenly attached to the coated surface and peeled off after 10 minutes, and found that there are no release of the coated film.

Comparative Example 14

The same test as in Example 43 was carried out, except that BANI-M was used instead of BANI-mX. A cellophane tape was evenly attached to the coated surface and peeled off after 10 minutes, and found that over 60% area of the coated film was peeled off together with the cellophane tape attached.

Comparative Example 15

The same test as in Example 43 was carried out, except that BANI-H was used instead of BANI-mX. A portion of the coated film was released in the thermostat. Thus, no cellophane tape attachment test could be carried out.

We claim:

1. An alkenyl-substituted bisnadimide represented by the following formula (1):

wherein $R^1$ and $R^2$ individually represent a hydrogen atom or a methyl group, and E is an alkylene.phenylene group or an alkylene.phenylene.alkylene group represented by the following formula (2):

(wherein a is an integer of 0 or 1, and $R^3$ and $R^{3'}$ individually represent a $C_1$–$C_4$ alkylene group or a $C_5$–$C_8$ cycloalkylene group).

2. The alkenyl-substituted bisnadimide according to claim 1, wherein $R^1$ and $R^2$ in formula (1) are a hydrogen atom, respectively.

3. The alkenyl-substituted bisnadimide according to claim 1, wherein E in formula (1) is selected from the group consisting of a phenylene.methylene group, a phenylene.ethylene group and a xylylene group.

4. The alkenyl-substituted bisnadimide according to claim 1, wherein $R^1$ and $R^2$ in formula (1) are a hydrogen atom, respectively, and E in formula (1) is selected from the group consisting of a phenylene.methylene group, a phenylene.ethylene group and a xylylene group.

5. The alkenyl-substituted bisnadimide according to claim 4, wherein E is a xylylene group.

* * * * *